United States Patent [19]

Perboni et al.

[11] Patent Number: 5,587,374
[45] Date of Patent: Dec. 24, 1996

[54] 10(1-HYDROXYETHYL)-11-OXO-1-AZATRI-CYCLO/7.2.0.0.$^{3,8}$/UNDEC-2-ENE-2-CARBOXYLIC ACID ESTERS AND A PROCESS FOR PREPARING THEREOF

[75] Inventors: Alcide Perboni, San Giorgio de Mantova; Tino Rossi, Verona; Giovanni Gaviraghi, Verona; Giorgio Tarzia, Verona; Antonella Ursini, Verona, all of Italy

[73] Assignee: Glaxo SpA, Verona, Italy

[21] Appl. No.: 388,515

[22] Filed: Feb. 14, 1995

Related U.S. Application Data

[62] Division of Ser. No. 264,239, Jun. 22, 1994, which is a continuation of Ser. No. 848,005, filed as PCT/EP91/01589 Aug. 20, 1991, abandoned.

[30] Foreign Application Priority Data

Aug. 21, 1990 [GB] United Kingdom ............... 9018330

Mar. 7, 1991 [GB] United Kingdom ............... 9104770

[51] Int. Cl.$^6$ ..................... C07D 487/00; A61K 31/395
[52] U.S. Cl. ............................................. 514/210; 540/302
[58] Field of Search ........................... 514/210; 540/302

[56] References Cited

U.S. PATENT DOCUMENTS 5,393,751  2/1995  Sendai et al. ..................... 540/302
5,407,931  4/1995  Tamburini et al. ................. 514/210

Primary Examiner—Rebecca Cook
Attorney, Agent, or Firm—Bacon & Thomas

[57] ABSTRACT

A compound of the formula 1-cyclohexyloxycarbonyloxyethyl (4S, 8S, 9R 10S, 12R)-4-methoxy-10-(1-hydroxyethyl)-11-oxo-1-azatricyclo[7.2.0.0.$^{3,8}$]undec-2-ene-2-carboxylate which is useful as a pharmaceutical composition to treat bacterial infection.

3 Claims, No Drawings

10(1-HYDROXYETHYL)-11-OXO-1-AZATRI-CYCLO/7.2.0.0.$^{3,8}$/UNDEC-2-ENE-2-CARBOXYLIC ACID ESTERS AND A PROCESS FOR PREPARING THEREOF

This application is a Division of application Ser. No. 08/264,239, filed Jun. 22, 1994 pending, which is a Continuation of application Ser. No. 07/848,005, filed May 20, 1992, now abandoned which is a continuation of PCT/EP91/01589 filed Aug. 20, 1991.

This invention relates to heterocyclic derivatives having antibacterial activity, to processes for their preparation, to compositions containing them and to their use in medicine.

Thus the present invention provides compounds of the general formula (I)

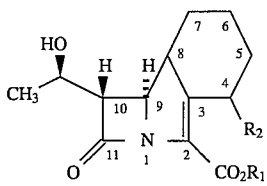

in which $R_1$ represents the group

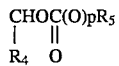

wherein $R_4$ represents a hydrogen atom or a $C_{1-4}$alkyl group; p is zero or one; $R_5$ represents a group selected from $C_{1-6}$alkyl, $C_{5-8}$cycloalkyl optionally substituted by a $C_{1-3}$alkyl group, phenyl, or $C_{1-4}$alkyl substituted by a $C_{1-3}$alkoxy group; and $R_2$ represents the group $OR_3$ in which $R_3$ represents a $C_{1-5}$alkyl group.

In addition to the fixed stereochemical arrangement as defined in formula (I) the molecule contains two further asymmetric carbon atoms at the 4 and 8 positions. Also the group $R_1$ contains at least one asymmetric carbon atom when $R_4$ is other than hydrogen. It will be appreciated that all stereoisomers including mixtures thereof arising from these additional asymmetric centres are within the scope of formula (I).

The general formula (I) as drawn includes at least 4 stereoisomers and mixtures thereof and these may be represented by the formulae (1a, 1b, 1c and 1d).

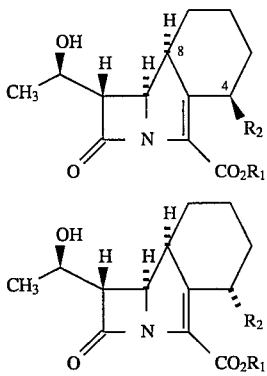

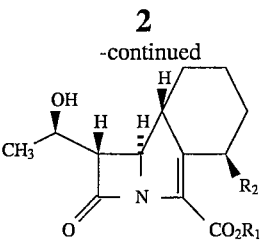

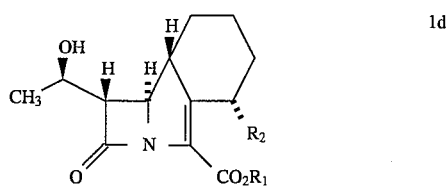

The wedge shaped bond ◀ indicates that the bond is above the plane of the paper. The broken bond ···· indicates that the bond is below the plane of the paper.

The configuration shown for the carbon atom at the 8-position in formulae 1a and 1b is hereinafter referred to as the β-configuration and in formulae 1c and 1d as the α-configuration.

The configuration shown for the carbon at the 4-position in formulae 1b and 1d is hereinafter-referred to as the α-configuration and in formulae 1a and 1c as the β-configuration.

In general, in the specific compounds named below, the β-configuration at the 8-position corresponds to the S isomer and the β-configuration at the 4-position to the R isomer. The α-configuration at the 8-position corresponds to the R isomer and the α- configuration at the 4-position corresponds to the S isomer. The assignment of the R or S configuration at the 4- and 8-positions has been made according to the rules of Cahn. Ingold and Prelog, Experientia 1956, 12, 81.

The term alkyl as used herein refers to a straight or branched chain alkyl group. When $R_4$ represents a $C_{1-4}$ alkyl group this may be for example methyl, ethyl, propyl, isopropyl or butyl.

When $R_5$ represents an alkyl group this may conveniently be a $C_{1-4}$alkyl group such as methyl, ethyl, isopropyl or t-butyl.

When $R_5$ represents a $C_{1-4}$alkyl group substitued by $C_{1-3}$alkoxyl, this may be for example a methyl, ethyl, propyl or isopropyl group substituted by methoxy.

When $R_5$ represents $C_{5-8}$cycloalkyl optionally substituted by $C_{1-3}$alkyl this may be for example a cyclopentyl, cyclohexyl, cycloheptyl or cyclooctyl group optionally substitued by a methyl or ethyl group.

A preferred class of compounds of formula (1) are those having the β-configuration at the 8-position. Within this class those having the α-configuration at the 4-position are particularly preferred.

A further preferred class of compounds of formula (I) are those wherein $R_4$ represents hydrogen, methyl, propyl or isopropyl, more particularly hydrogen or methyl.

Yet a further preferred class of compounds of formula (I) are those wherein $R_5$ represents a $C_{1-4}$alkyl group such as methyl, ethyl, isopropyl or t-butyl; a $C_{1-4}$alkyl group substituted by methoxy such as 1-methoxy-1-methylethyl; phenyl; or $C_{5-6}$ cycloalkyl group such as cyclopentyl or cyclohexyl optionally substituted by a methyl or ethyl group e.g. as in ethylcyclohexyl.

Compounds of formula (I) wherein $R_2$ is an ethoxy or methoxy group also represent a further preferred class of compounds according to the invention.

A particularly preferred group of esters according to the invention are those wherein $R_4$ represents a hydrogen atom or a methyl grouup, p is zero or 1 and $R_5$ represents a methyl, ethyl, isopropyl, t-butyl, 1-methoxy-1-methylethyl, phenyl, cyclohexyl, or 4-ethylcyclohexyl group.

A particularly preferred group of compounds according to the invention are those in which the carbon atom at the 8-position is in the β-configuration and the carbon atom at the 4-positon is in the α-configuration; $R_4$ represents a hydrogen atom or a methyl group; $R_5$ represents $C_{1-4}$alkyl, $C_{5-6}$cycloalkyl optionally substituted by a $C_{1-2}$alkyl group, phenyl, or $C_{1-4}$alkyl substituted by methoxy; p is zero or one and $R_2$ is methoxy.

Specific preferred compounds include esters of (4S, 8S, 9R, 10S, 12 R)-4-methoxy-10-(1-hydroxyethyl)-11-oxo-1-azatricyclo[7.2.0.0$^{3,8}$]undec-2-ene-2 carboxylic acid such as the pivaloyloxymethyl, 1-pivaloyloxyethyl, acetoxymethyl, 1-acetoxyethyl, 1-methoxy-1-methylethylcarbonyloxymethyl, 1-(1-methoxy-1-methylethylcarbonyloxy)ethyl, 1-benzoyloxyethyl, 1-isopropoxycarbonyloxyethyl, cyclohexyloxycarbonyloxymethyl, 1-(4-ethylcyclohexyloxycarbonyloxy)ethyl or more particularly 1-cyclohexyloxycarbonyloxyethyl ester.

Compounds according to the invention, when administered orally, exhibit a high level of antibacterial activity against a wide range of pathogenic microorganisms and they have a very high resistance to all β-lactamases. Compounds of the invention are also relatively stable to renal dehydropeptidase.

Compounds of the invention have been found to exhibit valuable levels of activity against strains of *Staphylococcus aureus, Streptococcus faecalis, Streptococcus pneumoniae, Escherichia coli, Klebsiella pneumoniae, Proteus mirabilis, Citrobacter freundii, Pseudomonas aeruginosa, Clostridium perfringens, Bacteriodes fragilis* and *Morganella morganii*.

The compounds of the invention may therefore be used for treating a variety of diseases caused by pathogenic bacteria in human beings and animals.

Thus, according to another aspect of the present invention, we provide a compound of formula (I) for use in the therapy or prophylaxis of systemic bacterial infections in a human or animal subject.

According to a further aspect of the invention we provide the use of a compound of formula (I) for the manufacture of a therapeutic agent for the treatment of systemic bacterial infections in human beings and animals.

According to a yet further aspect of the invention we provide a method of treatment of the human or non-human animal body to combat bacterial infections which method comprises administering to the body an effective amount of a compound of formula (I).

It will be appreciated by those skilled in the art that reference herein to treatment extends to prophylaxis as well as the treatment of established infections or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 200–2000 mg per day e.g. 1000 mg per day.

The desired dose may conveniently be presented in a single dose or as divided doses administered at appropriate intervals, for examaple as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation for oral administration comprising a compound of formula (I) together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The pharmaceutical compositions according to the invention may take the form of, for example, tablets or capsules prepared by conventional means with pharmaceutically acceptable excipients such as binding agents (e.g. pregelantinised maize starch, polyvinylpyrrolidone or hydroxypropylmethylcellulose), fillers (e.g. starch, lactose, micro-crystalline cellulose or calcium phosphate), lubricants (e.g. magnesium stearate, hydrogenated vegatable oils, talc, silica, polyethyleneglycols), disintegrants (e.g. potato starch or sodium starch glycolate), or wetting agents (e.g. sodium lauryl sulphate). Flow aids e.g. silicon dioxide may also be used if desired. The tablets may be coated by methods well know in the art.

Liquid preparations for oral administration may take the form of, for example, solutions, syrups or suspensions, or they may be presented as a dry product either for consitution with water or other suitable vehicle before use for administration as a liquid or for direct administration and then washed down with water or other suitable liquid. Such liquid preparations may be prepared by conventional means with pharmaceutically accepable additives such as suspending agents (e.g. sorbitol syrup, methyl cellulose or hydrogenated edible fats and oils such as hydrogenated castor oil), emulsifying or thickening agents (e.g. lecithin, aluminium stearate or acacia), non-aqueous vehicles (e.g. almond oil, fraetionated coconut oil, oily esters or ethyl alcohol), preservatives (e.g. methyl or butyl p-hydroxybenzoates or sorbic acid) and suitable flayouting and sweetening agents. Compounds of formula (I) may be prepared by esterification of the carboxylic acid (II)

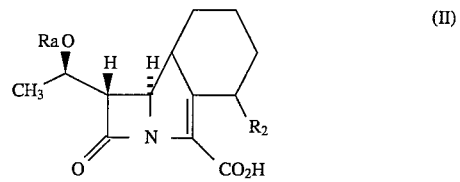

(II)

in which $R_a$ is hydrogen or a hydroxyl protecting group and $R_2$ is as defined for formula (I), or a salt or reactive derivative thereof and if required or desired subjecting the resulting compound prior to or subsequent to any separation into its sterochemical isomers, to removal of any protecting group $R_a$. When $R_a$ represents a hydroxyl protecting group this may be for example a hydrocarbylsilyl group such as trialkylsilyl e.g. trimethylsilyl or t-butyldimethysilyl.

The esterification of a compound of formula (II) or a salt thereof may be carried out by reaction with a compound $R_1X$ in which $R_1$ has the meanings defined above in formula (I) and X is a leaving group such a halogen atom, e.g. chlorine, bromine or iodine, or an alkyl or aryl sulphonate such as mesylate or tosylate, in the presence of a base. The reaction is preferably effected in the presence of a solvent, the nature of which is not critical, provided that it has no adverse effect upon the reaction. Suitable solvents include dimethylformamide, dimethylacetamide, or dimethylsulphoxide.

In one embodiment of this process the reaction is conveniently carried out using a salt such as an alkali metal salt e.g. potassium or sodium salt of the carboxylic acid (II) in the presence of a suitable quaternary ammonium salt such as triethyl benzylammonium chloride, trioctyl-methylammonium chloride or tetrabutylammonium bromide and preferably in the presence of a polar aprotic solvent such as dimethylformamide, dimethylacetamide or N-methylpyrrolidinone.

The esterification reaction may be conveniently carried out using a compound of formula (II) in which $R_a$ represents a hydrogen atom. If the esterfication reaction is carried out on a compound of formula (II) in which $R_a$ represents a hydroxyl protecting group then this group may be removed by conventional procedures. For example when $R_a$ is tert butyldimethylsilyl group this may be removed by treatment with tetrabutylammonium fluoride and acetic acid.

The compounds of formula (II) may be prepared by known methods e.g. as described in EP-A-0416953.

The compounds of formula (I) may also be prepared by the cyclisation of a compound of formula (III)

$$\text{(III)}$$

in which the groups $R_1$ and $R_2$ have the meanings defined for formula (I), $R_a$ is a hydroxyl protecting group and Y is an oxygen atom or a phosphine group, and if required or desired subjecting the resulting compound prior to or subsequent to any separation into its stereochemical isomers, to removal of the protecting group $R_a$.

The cyclisation of a compound of formula (III) in which Y is oxygen is conveniently carried out by heating in the presence of an organic phosphite. The reaction is preferably carried out in a solvent or mixture of solvents at a temperature within the range 60°–200°. Suitable solvents include hydrocarbons with an appropriate boiling point, for example aromatic hydrocarbons, such as toluene or xylene.

Suitable organic phosphites include acyclic and cyclic trialkylphosphites, triarylphosphites and mixed alkylarylphosphites. Particularly useful organic phosphites are the trialkylphosphites e.g. triethylphosphite or trimethylphosphite.

The cyclisation of a compound of formula (III) in which Y is a phosphine grouping is preferably carried out in a solvent at a temperature between 40°–200° C. Suitable solvents include hydrocarbons such as aromatic hydrocarbons, for example xylene or toluene,aliphatic hydrocarbons and halogenated hydrocarbons such as dichloromethane, chloroform and trichloroethane. Examples of suitable phosphine groups are triarylphosphines e.g. triphenyl phosphine or trialkylphosphines e.g. tri-t-butylphosphine.

The hydroxyl protecting group may be removed by well known standard procedures such as those described in Protective Groups in Organic Chemistry, pages 46–119, Edited by J F W McOmie (Plenum Press, 1973). For example when Ra is a tert butyldimethylsilyl group, this may be removed by treatment with tetrabutyl ammonium fluoride and acetic acid. This process is conveniently carried out in a solvent such as tetrahydrofuran. Similarly when the $R_a$ is trichloroethoxycarbonyl group this may be removed by treatment with zinc and acetic acid.

The compounds of formula (III) may be prepared by methods analogous to those described in EPA 0416953 for preparing structually related compounds.

In order that the invention may be more fully understood the following examples are given by way of illustration only.

In the Preparations and Examples, unless otherwise stated:

Melting points (m.p.) were determined on a Gallenkamp m.p. apparatus and are uncorrected. All temperatures refer to °C.

Infrared spectra were measured in chloroform-dl solutions on a FT-IR instrument. Proton Magnetic Resonance (1H-NMR) spectra were recorded at 300 MHz as solutions in chloroform-$d_l$. Chemical shifts are reported in ppm downfield ($\delta$) from $Me_4Si$, used as an internal standard, and are assigned as singlets (s), doublets (d), doublet of doublets (dd) or multipiers (m).

Column chromatography was carried out over silica gel (Merck AG Darmstadt, Germany).

Solutions were dried over anhydrous sodium sulphate.

"Petrol" refers to petroleum ether, b.p. 40°–60° C.

Methylene chloride was redistilled over calcium hydride; tetrahydrofuran was redistilled over sodium; ethyl ether was redistilled over sodium; xylene was redistilled over phosphorus pentoxide and ethyl acetate was dried over activated molecular sieves.

Intermediate 1

(2-Methoxy-2-methyl) propanoic acid ethenyl ester

To 2-methoxy-2-methylpropanoic acid (1.5 g), mercury (II) acetate (0.162 g), palladium acetate (0.0285 g), potassium hydroxide (0.067 g) and vinyl acetate (1.2 g) were added under nitrogen. The resulting solution was heated at 50° C. for 4 hrs. To the reaction mixture additional vinyl acetate (2.4 g) was then added and the mixture was heated at 50° C. for 16 hrs.

After cooling to 20° C., diethyl ether (15 ml) was added and the mixture was filtered on a pad of celite. The solution was washed with 10% sodium hydroxide solution (3×20 ml) and the aqueous phase was filtered on a pad of celite and then extracted with diethyl ether (2×70 ml). The organic phases were washed with brine (150 ml) and dried over anhydrous sodium sulphate to obtain the crude title compound as a pale yellow oil (0.7 g); tlc cyclohexane/ethyl acetate 8:2 Rf = 0.7; IR-($CDCl_3$) $V_{max}$ ($cm^{-1}$): 1749 (C=O ester) 1640 (C=C); 1H-NMR (300 $MH_z$; $CDCl_3$) (ppm) 7.30 (m), 4.983(dd), 4.648(dd), 3.297(s), 1.464(s).

Intermediate 2

(2-Methoxy-2-methyl) propanoic acid, 1-chloro ethyl ester

To a solution of the intermediate 1 (2.7 g) in ethyl acetate (50 ml) anhydrous hydrogen chloride was bubbled for 1 hr at 0° C., then nitrogen was bubbled for 10 minutes. The solvent was evaporated and the residue was purified through kugelrohr distillation (90° C./15 mmHg) to obtain the title compound as a colourless oil (2.1 g) Tlc cyclohexane/ethyl aceate 9:1. Rf= 0.9; IR ($CDCl_3$) $V_{max}$ ($cm^{-1}$): 1755 (C=O ester); 1H-NMR ($CDCl_3$; 300 $MH_z$) (ppm) 6.58 (q) 3.296(s), 1.837(d), 1.442(s).

Intermediate 3

(1-Chloro-2-methyl)propyl methyl carbonate

A solution of 1-chloro-2-methylpropyl chloroformate (1.71 g) in dry dichloromethane (5 ml) was added dropwise to a solution of methanol (0.83 ml) in dry dichloromethane (5 ml) at 0° C., under nitrogen, with stirring.

A solution of pyridine (0.80 ml) in dry dichloromethane (10 ml) was then added and the reaction mixture was stirred at 20° for 18 hrs. The mixture was diluted with dichloromethane 950 ml), washed with brine (3×40 ml), dried over anhydrous sodium sulfate and concentrated under a stream of nitrogen at low temperature, to afford the crude title compound as a colourless oil in quantitative yield.

H-NMR (300 MHZ, CDCl$_3$): 6.18(d), 3.86(s), 2.28-2.12(m), 1.08(d), 1.06 (d) ppm.

Intermediate 4

1-Chloroethyl 4-ethylcyclohexyl carbonate

A solution of 1-chloroethyl chloroformate (5.46 g) in dry dichloromethane (20 ml) was added dropwise, under nitrogen at 0°, to a stirred solution of 4-ethylcyclohexanol (5 g) in dry dichloromethane (20 ml) in presence of 3A molecular sieves. A solution of pyridine (3 g) in dry dichloromethane (20 ml) was added dropwise to the reaction mixture during 20 min at 0° the mixture was then warmed to 20°, stirred for 20 hours, washed with brine (2×50 ml) and dried. The solvent was removed under vacuum and the residue was distilled to give the title compound as a colourless oil (7.9 g; b.p. 130°/5.2 mbar; t.l.c. cyclohexane/ethyl acetate 9/1 Rf=0.88; IR (CDCl3), Vmax (cm-1): 1757 (C=O); 1H-NMR (300 MHz, CDCl3): 6.43 (q), 6.42 (q), 4.93 (bs), 4.59 (tt), 2.14-2.01 (bs), 2.00-1.88 (bs), 1.88-1.78 (m), 1.83 (d), 1.82 (d), 1.60-1.50 (m), 1.50-1.32 (m), 1.30-1.15 (m), 1.28-1.18 (m) 1.05-0.95 (m), 0.95-0.85 (m).

Intermediate 5

1-Chloro-2-methylpropyl 2,2-dimethypropionate

2-Methylpropionaldehyde (5.98 g) was added dropwise, during 10 min., to a stirred mixture of zinc chloride (0.11 g) and pivaloyl chloride (10 g), under nitrogen at −20°. The reaction mixture was then warmed to 23° and stirred for further 2 hours. The solid was removed by centrifugation and the oily residue was distilled to obtain the title compound as a colourless oil (11.55 g; b.p. 70°/35 mbar; IR (CDCl3, Vmax (cm-1): 1749 ( C=O ); 1H-NMR (300 MHz, CDCl3 ): 6.28 (d), 2.16 (m), 1.22 (s), 1.05 (d) ppm.

Intermediate 6

Cyclohexyl chloromethyl carbonate

A stream of chlorine was slowly bubbled into cold (−10/+5°) methyl chloroformate (6 ml) under diffuse light. The reaction was monitored by 1H-NMR and stopped before the dichloromethyl chloroformate concentration became more than 5% molar. Nitrogen was bubbled through the solution until it became colourless and the residue was distilled to obtain two main fractions containing the required intermediate chloromethyl chloroformate; fraction a (2.48 g; molar ratio: methyl chloroformate/chloromethyl chloroformate/dichloromethyl chloroformate 19/77/4), fraction b (1.76 g; molar ratio: methyl chloroformate/chloromethyl chloroformate/dichloromethyl chloroformate 4/90/6). To an ice cold solution of cyclohexanol (1.37 ml) in dry dichloromethane (5 ml), in presence of 3A molecular sieves and under nitrogen, a solution of the (fraction a) (1.7 g) in dry dichloromethane (5 ml) was added during 5 min. A solution of pyridine (1.06 ml) in dry dichloromethane (5 ml) was then added to the reaction mixture during 30 min. at 0°, and the mixture was slowly warmed to 20°–25°. After 5 hours, the solution was filtered, diluted with dichloromethane (30 ml) , washed with water (20 ml), brine (3×30 ml) and dried. The solvent was distilled off and the residue was purified by column chromatography on silic a gel, using cyclohexane/ethyl acetate 9/1 as eluant, to obtain the title compound as a white wax (1.98 g; t.l.c. cyclohexane/ethyl acetate 9/1 Rf=0.44; IR (CDCl3), Vmax (cm-1): 1759 (C=O); 1H-NMR (300 MHz, CDCl3): 5.73 (s), 4.78-4.66 (m), 2.00-1.90 (m), 1.80-1.70 (m), 1.60-1.20 (m) ppm).

EXAMPLE 1

1-(Cyclohexyloxycarbonyloxy)ethyl (4S,8S,9R,10S,12R)-4-methoxy-10-(1'-hydroxyethyl)-11-oxo-1-azatricyclo-[7.2.0.0$^{3,8}$]undec-2-ene-2-carboxylate To a solution of potassium (4S,8S,9R,10S,12R)-4-methoxy-10-(1-hydroxyethyl)-11-oxo-1-azatricyclo [7.2.0.0$^{3,8}$] undec-2-ene-2-carboxylate (hereinafter referred to as "Intermediate A") (0.5 g) in dimethylformamide (8 ml) tetrabutylammonium bromide (0.5 g) and (1-chloroethyl)-cyclohexyl carbonate (0.65 g) were added at 22°. The resulting mixture was stirred at 22° for 15 hr, then poured into diethyl ether (60 ml), washed with 1% aq HCl (40 ml), 5% aq NaHCO3 (2×50 ml) and brine (2×50 ml), dried and concentrated. The residue (1 g) was dissolved in diethyl ether (2 ml) and light petroleum (20 ml) added with vigorous stirring. The precipitate (0.1 g) was filtered off and the mother liquors were concentrated to give a residue, which was dissolved in diethyl ether (1 ml) and light petroleum (20 ml) added under vigorous stirring to give more precipitate (0.14 g). The precipitates were combined (0.24 g) and further purified by dissolution in diethyl ether (3 ml) and precipitation from light petroleum (30 ml) under vigorous stirring to obtain the title compound as a white powder (0.160 g; t.l.c. diethyl ether Rf 0.44, m.p. 90°–100°).

IR (CDCl3) Vmax (cm-1) 1771, 1632; 1H-NMR (300 MHZ, CDCl3) 6.93-6.85 (q+q), 4.92(t), 4.64(m), 4.25-4.05(m), 3.30-3.15(m), 3.25(s), 3.24(s), 2.08(m), 2.0-1.2(m), 1.61(d), 1.59 (d), 1.31(d), 1.30(d).

According the experimental procedures described in the Example 1, the following esters were prepared from Intermediate A.

EXAMPLE 2

1 - (Ethyloxycarbonytoxy) ethyl (4S,8S,9R,10S,12R)-4-methoxy-10-(1'-hydroxyethyl)-11-oxo-1-azatricyclo-[7.2.0.0$^{3,8}$]undec-2-ene-2-carboxylate was obtained as an oil ( t.l.c. diethyl ether Rf 0.42).

IR (CDCl3) Vmax (cm-1) 1765, 1738, 1608; 1H-NMR (300 MHZ, CDCl3) 6.93-6.87(q+q), 4.933(m), 4.3-1.8(m), 3.26-3.24(s+s), 3.32-3.20(m), 2.08(m), 1.94-1.3(m), 1.62 (d), 1.60(d), 1.36-1.28(m) from Intermediate A and (1-chloroethyl)-ethyl carbonate.

EXAMPLE 3

1-(Isopropyloxycarbonyloxy)ethyl (4S,8S,9R,10S,12R)-4-methoxy-10-(1'-hydroxyethyl)-11-oxo-1-azatricyclo-[7.2.0.0$^{3,8}$]undec-2-ene-2-carboxylate IR (CDCl3) Vmax (cm-1) 3614, 1767, 1632; 1H-NMR (300 MHZ, CDCl3) 6.90(q), 6.89(q), 4.95-4.83(m), 4.3-4.2(m), 4.191(dd), 3.35-3.20(m), 3.257(s), 3.243(s), 2.07(m), 1.93-1.75(m), 1.7-1.3 (m), 1.613(d), 1.33-1.29(d+d+d), t.l.c. cyclohexane, ethyl acetate 4:6 Rf 0.4 was obtained from Intermediate A and (1-chloroethyl)-isopropyl carbonate.

EXAMPLE 4

1-(Acetoxy)ethyl (4S,8S,9R,10S,12R)-4-methoxy-10-(1'-hydroxyethyl)-11-oxo-1-azatricyclo-[7.2.0.0$^{3,8}$]undec-2-ene-2-carboxylate was obtained as an oil (0.160 g; t.l.c. cyclohexane, ethyl acetate 4:6 Rf 0.4) IR (CDCl3) Vmax (cm-1) 3605, 1769, 1700; 1H-NMR (300 MHZ, CDCl3) 6.99(q), 6.98(q), 4.93(t), 4.25(m), 4.19(dd), 3.3-3.2(m), 3.25(s), 3.24(s), 2.10(s), 2.07(s), 2.08(m), 1.95-1.3 (m), 1.56 (d), 1.55 (d), 1.31 (d), 1.30(d) from Intermediate A and (1-chloroethyl)acetate.

EXAMPLE 5

1-(Cyclohexylcarbonyloxy) ethyl
(4S,8S,9R,10S,12R)-4-methoxy-10-(1'-hydroxyethyl)-
11-oxo-1-azatricyclo-[7.2.0.0$^{3,8}$]undec-
2-ene-2-carboxylate IR (CDCl3) Vmax (cm-1) 1774, 1750, 1630; 1H-NMR (300 MHZ, CDCl3) 6.997(q), 6.977(q), 4.931(t), 4.913(t), 4.24(m), 4.193(dd), 3.3-3.2(m), 3.25(s), 3.245(s), 2.38-2.24(m), 2.05(m), 1.95-1.2(m), 1.65 (dd), 1.566(d), 1.555(d), 1.326(d), 1.314(d) was obtained from Intermediate A and (1-chloroethyl) cyclohexanecarboxylate.

EXAMPLE 6

1-(Benzoyloxy)ethyl (4S,8S,9R, 10S,12R)-4-methoxy-10-(1'-hydroxyethyl)-11-oxo-1-azatricyclo[7.2.0.0$^{3,8}$]undec-2-ene-2-carboxylate was obtained as an oil (0.045 g; t.l.c. cyclohexane, ethyl acetate 1:1 Rf 0.25);

IR (CDCl3) Vmax (cm-1) 1776, 1738, 1640, 1603; 1H-NMR (300 MHZ, CDCl3) 8.1-8.02(m), 7.58(tt), 7.48-7.4(m), 7.27(m), 4.948(t), 4.914(t), 4.3-4.2(m), 4.20(dd), 3.3-3.2(m), 3.23(s), 3.21(s), 2.05(m), 1.9-1.3(m), 1.725 (d), 1.708(d), 1.326(d), 1.302(d) from Intermediate A and (1-chloroethyl)-benzoate.

EXAMPLE 7

1-[(1,1-Dimethylethyl)carbonyloxy]ethyl (4S,8S,9R,10S, 12R)-4-methoxy-10-(1'-hydroxyethyl)-11-oxo-1-azatricyclo[7.2.0.0$^{3,8}$]undec-2-ene-2-carboxylate was obtained as an oil ( 0.160 g; t.l.c. cyclohexane, ethyl acetate 4:6 Rf 0.37); IR (CDCl3) Vmax (cm-1) 3666, 1776, 1744, 1632; 1H-NMR (300 MHZ, CDCl3) 6.982(q), 6.941(q), 4.94-4.88(m), 4.3-4.16(m), 3.3-3.18(m), 3.238(s), 3.20(s), 2.05(m), 1.9-1.2(m), 1.565(d), 1.554(d), 1.317 (d), 1.306 (d), 1.207 (s), 1.179 (s) from Intermediate A and 1-[(1,1-dimethylethyl) carbonyloxy]ethyl chloride.

EXAMPLE 8

1-[2-Methoxy-2-methyl-propanoyloxy)]ethyl (4S, 8S, 9R,10S, 12R)-4-methoxy-10-(1'-hydroxyethyl)-11-oxo-1-azatricyclo[7.2.0.0$^{3,8}$]undec-2-ene-2-carboxylate was obtained as an oil (0.130 g; t.l.c. diethyl ether Rf 0.35); IR (CDCl3) Vmax (cm-1) 1772, 1603; 1H-NMR (300 MHZ, CDCl3) 7.028(q), 6.984(q), 4.914(m), 4.3-4.2(m), 4.190(dd), 3.3-3.2(m), 3.260(s), 3.248(s), 3.290(s), 3.226(s), 2.06(m), 1.9-1.35(m), 1.604(m), 1.437(s), 1.429(s), 1.403(s), 1.400(s), 1.315(d) from Intermediate A and 2-methoxy-2-methyl-propanoic acid chloroethyl ester.

EXAMPLE 9

Acetoxymethyl (4S,8S,9R,10S,12R)-4-methoxy-10-(1'-hydroxyethyl)-11-oxo-1-azatricyclo[7.2.0.0$^{3,8}$]undec-2-ene-2-carboxylate was obtained as an oil (0.240 g; t.l.c. cyclohexane, ethyl acetate 4:6 Rf 0.24); IR (CDCl3) Vmax (cm-1) 1769, 1730, 1640; 1H-NMR (300 MHZ, CDCl3) 4.996(t), 4.802(s), 4.3-4.2(m), 4.23 (dd), 3.774(s) 3.36-3.24 (m+dd), 3.28 (s), 2.1 (m), 1.94-1.30 (m), 1.769 (d), 1.327 (d) from Intermediate A and chloromethyl acetate.

EXAMPLE 10

[(1,1-Dimethyl-ethyl)carbonyloxy]methyl (4S,8S, 9R, 10S, 12R) -4-methoxy-10-(1'-hydroxyethyl)-11-oxo-1-azatricyclo[7.2.0.0$^{3,8}$]undec-2-ene-2-carboxylate was obtained as an oil (0.260 g; t.l.c. cyclohexane, ethyl acetate 1:1 Rf 0.26); IR (CDCl3) Vmax (cm-1) 3569, 1772, 1751, 1600; 1H-NMR (300 MHZ, CDCl3) 5.95(d), 5.85(d), 4.88(t), 4.24(m), 4.20(dd), 3.27(m), 3.25(dd), 3.23(s), 2.1(m), 2.0(bs), 1.95-1.6(m), 1.5-1.20(m), 1.31 (d), 1.21 (s) from Intermediate A and [(1,1-dimethylethyl)carbonyloxy] methyl iodide.

EXAMPLE 11

1-(2-Methoxy-2-methyl-propanoyloxy)methyl (4S,8S,9R, 10S,12R)-4-methoxy-10-(1'-hydroxyethyl)-11-oxo-1-azatricyclo[7.2.0.0$^{3,8}$]undec-2-ene-2-carboxylate was obtained as an oil (0.110 g; t.l.c. diethyl ether Rf 0.33); IR (CDCl3) Vmax (cm-1) 3600, 1772, 1740, 1640; 1H-NMR (300 MHZ, CDCl3) 5.964(d+d), 4.904(m), 4.242(m), 4.203(dd), 3.984(dd), 3.33-3.22 (m+dd), 3.292(s), 3.240(s), 2.1(m), 1.95-1.2(m), 1.441(s), 1.429(s), 1.315(s) from Intermediate A and (2-methoxy-2methyl) propanoic acid chloromethylester.

EXAMPLE 12

1- (Methyloxycarbonyloxy)-2-methylpropyl (4S,8S,9R, 10S,12R)-4-methoxy-10-(1'-hydroxyethyl)-11-oxo-1-azatricyclo[7.2.0.0$^{3,8}$]undec-2-ene-2-carboxylate was obtained as an oil, (0.040 g; t.l.c. cyclohexane, ethyl acetate 4:6 Rf 0.36); IR (CDCl3) Vmax (cm-1) 1767, 1734, 1680; 1H-NMR (300 MHZ, CDCl3) 6.661(d), 6.636(d), 4.974(m), 4.936(m), 4.3-4.15(m), 3.824(s), 3.805(s), 3.262(s), 3.242(s), 3.32-3.18(m), 1.327(d), 1.306(d), 1.15-0.95(m), 2.4-1.2(m) from Intermediate A and (1-chloro-2methyl)propylmethylcarbonate.

EXAMPLE 13

1-(Acetyloxy)butyl (4S,8S,9R,10S,12R)-4-methoxy-10-(1'-hydroxyethyl)-11-oxo-1-azatricyclo[7.2.0.0$^{3,8}$]undec-2-ene-2-carboxylate was obtained as an oil (0. 050 g; t.l.c. cyclohexane, ethyl acetate 1:1 Rf 0.33); IR (CDCl3) Vmax (cm-1) 1769, 1732, 1632; 1H-NMR (300 MHZ, CDCl3) 6.925(q), 4.948(m), 4.28-4.16(m), 3.3-3.2(m), 3.251 (s), 3.243 (s), 2.105(s), 2.069(s), 2.12-2.04(m), 1.94-1.74(m), 1.74-1.58 (m), 1.54-1.349m), 1.318(d), 1.307(d), 0.962(t), 0.957(t) from Intermediate A and 1-bromobutyl acetate.

EXAMPLE 14

1-[(4-ethylcyclohexyloxy)carbonyloxy]ethyl
(4S,8S,9R,10S,12R)-4-methoxy-10-(1'-hydroethyl)-
11-oxo-1-azatri
cyclo[7.2.0.0$^{3,8}$]undec-2-ene-2-carboxylate To a solution of the Intermediate A (0.3 g) in N,N-dimethylformamide (5 ml), tetra-n-butylammonium bromide (0.3 g) and the intermediate 4 (0.47 g) were added under nitrogen and stirring was continued for 16 h at 22°. The reaction mixture was diluted with diethylether (15 ml), washed with saturated ammonium chloride (2×20 ml), brine (2×20 ml), dried and evaporated in vacuo. The oily residue was chromatographed on silica gel, using cyclohexane/ethyl acetate 7/3 as eluant, to obtain the title comopund as a white foam (0.169 g; t.l.c. cyclohexane/ethyl acetate 1/1 Rf =0.41; IR (CDCl3), Vmax (cm-1): 3640 (OH), 1761 (C=O), 1634 (C=C); 1H-NMR (300 MHz, CDCl3 ): 6.88 (m) , 4.92 (m), 4.91 (m), 4.95-4.85 (m),4.54 (m), 4.28-4.18 (m), 4.18 (dd), 3.30-3.20 (m), 3.24 (s), 3.23 (s), 2.05 (m) , 2.00-1.75 (m) , 1.70-1.50 (m), 1.60 (m), 1.50-1.09 (m), 1.31 (d), 1.29 (d), 1.25-1.15 (m), 0.86 (m)ppm)

EXAMPLE 15

Cyclohexyloxycarbonyloxy)methyl (4S,8S,9R,10S,12R)-4-methoxy-10-(1'-hydroxyethyl)-11-oxo-1-azatricyclo[7.2.0.0$^{3,8}$]undec- 2-ene-2-carboxylate To a solution of the Intermediate A (0.22 g) in N,N-dimethylformamide (6.5 ml), in presence of 3A molecular sieves, tetra-n-butylammonium bromide (0.222 g) and the intermediate 6 (0.191 g) were added. The resulting mixture was stirred at 22° for 5 hours, diluted with diethylether (50 ml), washed with water (30 ml), saturated ammonium chloride (2×30 ml), 5% aq sodium hydrogen carbonate (30 ml), brine (2×30 ml), water (30 ml) and dried. The solvent was removed under vacuum and the residue was purified by column chromatography on silica gel, using cyclohexane/ethyl acetate 100/0 to 65/35, to obtain the title compound as a white foam (0.1 g; t.l.c. cyclohexane/ethyl acetate 1/1 Rf=0.18; IR (CDCl3), Vmax (cm-1): 3614 (OH), 1772 (C=O β-lactam) , 1717 (C=O ester) , 1640 (C=C); 1H-NMR (300 MHz, CDCl3): 5.90 (dd), 4.93 (t), 4.67 (m), 4.30-4.20 (m), 4.20 (dd), 3.35-3.25 (m), 3.25 (s), 2.08 (m), 2.00-1.80 (m), 1.80-1.30 (m), 1.32 (d) ppm).

EXAMPLE 16

1-[(1,1-dimethylethyl)carbonyloxy]-2-methylpropyl (4S,8S,9R,10S,12R)-4-methoxy-10-(1'-hydroxyethyl)-11-oxo-1-azatricyclo[7.2.0.0$^{3,8}$]undec-2-ene-2-carboxylate To a solution of the Intermediate A (0.3 g) in N,N-dimethylformamide (5 ml), tetra-n-butylammonium bromide (0.3 g) and the intermediate 5 (0.398 g) were added under nitrogen and stirring was continued for 16 h at 22°. The reaction mixture was diluted with diethylether (15 ml), washed with saturated ammonium chloride (2×30 ml), brine (2×30 ml), dried, and evaporated in vacuo. The oily residue was chromatographed on silica gel, using cyclohexane/ethyl acetate 7/3 as eluant, to obtain the title compound as a colourless oil (0.057 g; t.l.c. cyclohexane/ethyl acetate 1/1 Rf=0.45; IR (CDCl3) , Vmax (cm-1): 3611 (NH), 1774 (C=O βlactam) , 1747 (C=O ester), 1632 (C=C); 1H-NMR (300 MHz, CDCl3 ): 6.76 (d), 6.72 (d) , 4.95 (t), 4.92 (t), 4.30-4.16 (m), 3.32-3.19 (m), 3.24 (s), 3.23 (s), 2.10 (m), 2.06 (m), 1.94-1.80 (m), 1.75-1.60 (m), 1.50-1.20 (m), 1.32 (d), 1.31 (d), 1.22 (s), 1.19 (s), 1.06-0.98 (d) ppm)

EXAMPLE 17

1- (Cyclohexyloxycarbonyloxy)ethyyl (4S,8S,9R,10S,12R)-4-methoxy-10-(1'-hydroxyethyl)-11-oxo-1-azatricyclo-[7.2.0.0$^{3,8}$]undec-2-ene-2-carboxylate To a solution of sodium (4S,8S,9R,12R)-4-methoxy-10-(1-hydroxyethyl)-11-oxo-1-azatricyclo[7.2.0.0$^{3,8}$]undec-2-ene-2-carboxylate (194 mg) in dimethylformamide (8 ml) triethylbenzylammonium chloride (146 mg) and (1-chloro-ethyl)-cyclohexyl carbonate (0.142 ml) were added at room temperature. The resulting mixture was stirred at 600 for 97 min, diluted with diethyl ether (30 ml) and washed with cold water (60 ml). The aqueous layer was re-extracted with diethyl ether (30 ml) and the combined organic phases were washed with brine (30 ml) and dried over sodium sulphate. The organic layer was concentrated under reduced pressure and the resultant white foam (288 mg) was crystallised from diethyl ether/petroleum to give the title compound (220 mg) as a white solid.

PHARMACY EXAMPLES

Tablets

Example A

|  | mg/tab |
| --- | --- |
| Compound of Example 1 | 320 |
| Lactose | 150 |
| Ethyl cellulose | 20 |
| Sodium lauryl sulphate | 7 |
| Magnesium stearate | 3 |
| Tablet core | 500 mg |

The active ingredient and the lactose are blended together and then granulated using water as the granulating fluid. The dried granules are blended with the ethyl cellulose, sodium lauryl sulphate and magnesium stearate and the tablet core formed using an appropriate punch. The tablet may then be coated using conventional techniques and coatings.

Example B

|  | mg/tab |
| --- | --- |
| Compound of Example 1 | 320 |
| Compressible sugar | 170 |
| Sodium lauryl sulphate | 7 |
| Magnesium stearate | 3 |
| Tablet core | 500 |

The active ingredient and the excipients are blended together and then compressed using an appropriate punch. If required the tablet thus formed may be coated in a conventional manner.

Granules

Example C

|  | mg/unit dose |
| --- | --- |
| Compound of Example 1 | 320 |
| Starch | 100 |
| Cellulose | 40 |
| Polymethacrylate | 30 |
| Sodium lauryl sulphate | 7 |
| Magnesium stearate | 3 |
| Flavouring agent | qs |

Example D

| | mg/unit dose |
|---|---|
| Compound of Example 1 | 320 |
| Ethyl cellulose | 140 |
| Polymethacrylate | 30 |
| Sodium lauryl sulphate | 7 |
| Magnesium stearate | 3 |
| Flavouring agent | qs |

Example E

| | mg/unit dose |
|---|---|
| Compound of Example 1 | 320 |
| Compressible sugar | 140 |
| Polymethacrylate | 30 |
| Sodium laurylsulphate | 7 |
| Magnesium & stearate | 3 |
| Flavouring agent | qs |

A solution of the active ingredient in ethanol is sprayed into a suitable fluid bed granulator charged with the major excipients. The granules so formed are dried and screened. If desired the granules may then be coated with a suitable enteric coating and dried. The dried granules are then blended with the remaining excipients including any flavouring agent and coated, for example with an enteric coating. The granules thus obtained may be filled into capsules or the like for a single dose presentation or filled into bottles for subsequent preparation of a multi dose oral liquid presentation.

Activity Data

In conventionally conducted protection tests using mice, orally administered compounds of the invention exhibited very high activity against pathogenic bacteria, as illustrated in the following table, where compounds are compared with the known orally administrable broad spectrum antibiotic cefuroxime axetil:

| Compound | $ED_{50}$ (mg/kg) | |
|---|---|---|
| | Staph. aureus | E. Coli |
| Example 1 | <1 | <1 |
| Example 3 | <1 | <1 |
| Example 10 | <1 | <1 |
| Cefuroxime axetil | 6 | 26 |

The compounds of the invention are also essentially non-toxic at therapeutically useful dose levels. For example, no adverse effects were observed when the compound of Example 1 was orally administered to mice at doses up to 1000 mg/kg.

We claim:

1. 1-Cyclohexyloxycarbonyloxethyl (4S,8S,9R,10S,12R)-4-methoxy-10-(1-hydroxyethyl)-11-oxo-1-azatricyclo[7.2.0.0.$^{3,8}$]undec-2-ene-2-carboxylate.

2. A Pharmaceutical composition comprising a compound as claimed in claim 1 in admixture with one or more pharmaceutically acceptable carriers or excipients.

3. A method of treatment of a human or non-human animal body to combat bacterial infections comprising administration to said body of an effective amount of a compound as claimed in claim 1.

* * * * *